(12) United States Patent
Ein-Gal

(10) Patent No.: US 6,416,514 B1
(45) Date of Patent: Jul. 9, 2002

(54) ELECTROCOAGULATION APPARATUS

(76) Inventor: Moshe Ein-Gal, 30 Azar Street, Ramat Hasharon (IL), 47203

( * ) Notice: Subject to any disclaimer, the term of this patent is extended or adjusted under 35 U.S.C. 154(b) by 0 days.

(21) Appl. No.: 09/383,455

(22) Filed: Aug. 26, 1999

(30) Foreign Application Priority Data

Aug. 30, 1998 (IL) .................................................. 125990

(51) Int. Cl.$^7$ ............................................ A61B 18/18
(52) U.S. Cl. ........................................................ 606/49
(58) Field of Search ................................ 606/40–49, 50; 607/148, 166, 115, 100, 101; 604/22, 20

(56) References Cited

U.S. PATENT DOCUMENTS

| | | | | |
|---|---|---|---|---|
| 3,612,061 A | * | 10/1971 | Collins ..................... | 340/407.1 |
| 4,211,230 A | * | 7/1980 | Woltosz ..................... | 606/40 |
| 4,837,049 A | * | 6/1989 | Byers et al. ................. | 437/96 |
| 5,047,028 A | | 9/1991 | Qian ........................... | 606/49 |
| 5,403,311 A | * | 4/1995 | Abele et al. ................ | 606/49 |
| 5,437,664 A | | 8/1995 | Cohen et al. | |
| 5,449,378 A | * | 9/1995 | Schouenborg ............... | 607/46 |
| 5,658,282 A | | 8/1997 | Daw et al. | |
| 5,674,267 A | * | 10/1997 | Mir et al. .................... | 607/72 |
| 5,707,349 A | * | 1/1998 | Edwards ...................... | 604/22 |
| 5,817,049 A | * | 10/1998 | Edwards ...................... | 604/22 |
| 6,009,347 A | * | 12/1999 | Hofmann ..................... | 604/21 |

FOREIGN PATENT DOCUMENTS

| | | |
|---|---|---|
| CH | 684157 A5 | 7/1994 |
| WO | WO 95/29644 | 11/1995 |

* cited by examiner

Primary Examiner—Michael Peffley
(74) Attorney, Agent, or Firm—Dekel Patent Ltd.; David Klein

(57) ABSTRACT

Electrocoagulation apparatus including an array of more than two RF energized needles, and an RF generator for selectively energizing at least two of the needles so that energy passes therebetween. The needles may be arranged in rows, and the rows may be staggered. Alternatively, the needles may be arranged in a matrix of rows and columns. The needles may be generally equally spaced from each other or randomly arranged. Preferably the needles are spaced from each other corresponding to a width of a vein.

11 Claims, 2 Drawing Sheets

ELECTROCOAGULATION APPARATUS

FIELD OF THE INVENTION

The present invention relates generally to apparatus and method for electrocoagulation, and particularly to electrocoagulation of varicose veins.

BACKGROUND OF THE INVENTION

Many treatments of varicose veins are known. These treatments may be divided into two large categories, surgical and non-surgical. Surgical methods include, among others, removal of veins, ligation of veins and induced constriction of veins so as to re-direct flow of blood to alternate, non-varicose veins. The latter form of treatment includes electrically induced coagulation, also called electrocoagulation.

Prior art methods for electrocoagulation of veins include German Patent 4,414,807 which describes an electrosurgical instrument for localized varicose vein coagulation. The instrument has two fork-like protruding needle electrodes which may be inserted into a vein. High frequency current is then supplied to the electrodes, thereby causing coagulation of the vein.

Swiss Patent 684,157 describes an electrocoagulation instrument for localized varicose vein coagulation. The instrument has a heated electrode which includes a long tubular metal needle covered with a thermo-resistant insulating material. As in the previous patent, the electrodes may be inserted into a vein and high frequency current may be applied thereto to cause coagulation of the vein.

U.S. Pat. No. 5,047,028 describes a balloon catheter for electrocoagulation of varicose veins. The balloon catheter is introduced into a body cavity of a vein site and includes a plating wire which forms one electrode. A second electrode consists of a large plate placed on the chest of a patient. Electrical connection between the electrodes is made by filling the balloon with a conducting expansion fluid, preferably a liquid or gel-like medication vehicle charged with a medication. The balloon has a wall which is semipermeable to the conducting fluid. The expansion fluid upon permeating the wall, ensures a fixed electrical resistance between the second electrode and the surface of the body cavity.

SUMMARY OF THE INVENTION

The present invention seeks to provide novel apparatus and methods for electrocoagulation. Although the present invention will be described with reference to electrocoagulation of varicose veins, it is appreciated that electrocoagulation of other vessels, growths, tumors or organs is in the scope of the present invention.

In accordance with a preferred embodiment of the present invention, an array of RF energized needles are arranged in an orderly or random fashion on a substrate of a ringed housing. The needles are pressed against a site to be electrocoagulated, such as a site of varicose veins. Pairs of needles are energized in any pattern by an RF generator. The pairs of needles act as electrodes and the energy that passes between the needles causes electrocoagulation of the vein site. Any pattern of varicose veins may be electrocoagulated, unlike the prior art which merely uses a pair of needles which may be ineffective in treating complicated clusters of varicose veins.

There is thus provided in accordance with a preferred embodiment of the present invention electrocoagulation apparatus including an array of more than two RF energized needles, and an RF generator for selectively energizing at least two of the needles so that energy passes therebetween. The needles may be arranged in rows, and the rows may be staggered. Alternatively, the needles may be arranged in a matrix of rows and columns. The needles may be generally equally spaced from each other or randomly arranged. Preferably the needles are spaced from each other corresponding to a width of a vein.

In accordance with a preferred embodiment of the present invention the needles are attached to a ring which at least partially circumscribes the needles.

Further, in accordance with a preferred embodiment of the present invention the ring includes a strap attachable to a limb of a patient.

Still further in accordance with a preferred embodiment of the present invention at least one of the needles is hollow to allow passage therethrough of a substance.

There is also provided in accordance with a preferred embodiment of the present invention a method for electrocoagulation including placing an array of more than two RF energized needles against epidermis of a patient at a site to be electrocoagulated, selecting at least two of the needles to pass energy therebetween, and transmitting RF energy to tips of the selected needles so as to cause electrocoagulation at the site.

In accordance with a preferred embodiment of the present invention the step of placing includes pressing the needles against the epidermis so as to cause a vein to be located between tips of adjacent needles.

Further in accordance with a preferred embodiment of the present invention the step of placing includes pressing the needles against the epidermis so as to cause the epidermis to bulge inwards of a space formed between tips of adjacent needles.

Still further in accordance with a preferred embodiment of the present invention the needles are arranged in rows and the step of transmitting includes energizing pairs of the needles, the pairs including two needles selected from the same row.

Additionally in accordance with a preferred embodiment of the present invention the needles are arranged in rows and the step of transmitting includes energizing pairs of the needles, the pairs including two needles selected from different rows.

Further in accordance with a preferred embodiment of the present invention the step of transmitting includes energizing pairs of the needles in a zigzag pattern.

In accordance with a preferred embodiment of the present invention, the transmitting of RF energy includes a high frequency shaped train of pulses, typically, but not necessarily, in the range of 200 KHz to 1 MHz, and preferably with an intensity of up to 100 W. Preferably the duration of the pulses is approximately 10–40 msec, the duration changing in correspondence with the frequency and intensity of the pulses.

Additionally in accordance with a preferred embodiment of the present invention, RF energy is transmitted to a site downstream of the electrocoagulation site.

Further in accordance with a preferred embodiment of the present invention, a substance may be introduced through the RF energized needle, for example, a coagulating agent and a substance which enhances electrical flow.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
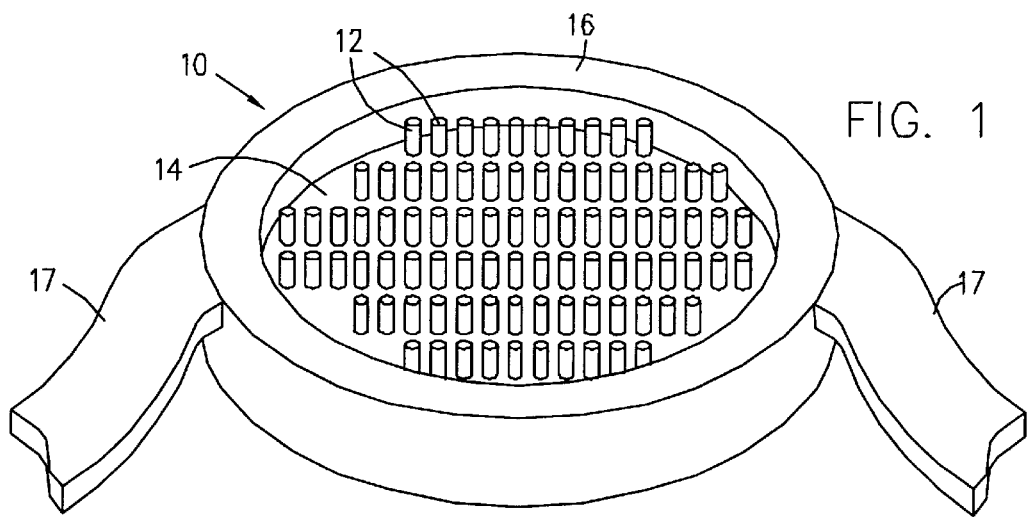
FIG. 1 is a simplified illustration of electrocoagulation apparatus constructed and operative in accordance with a preferred embodiment of the present invention.
Figure 2:
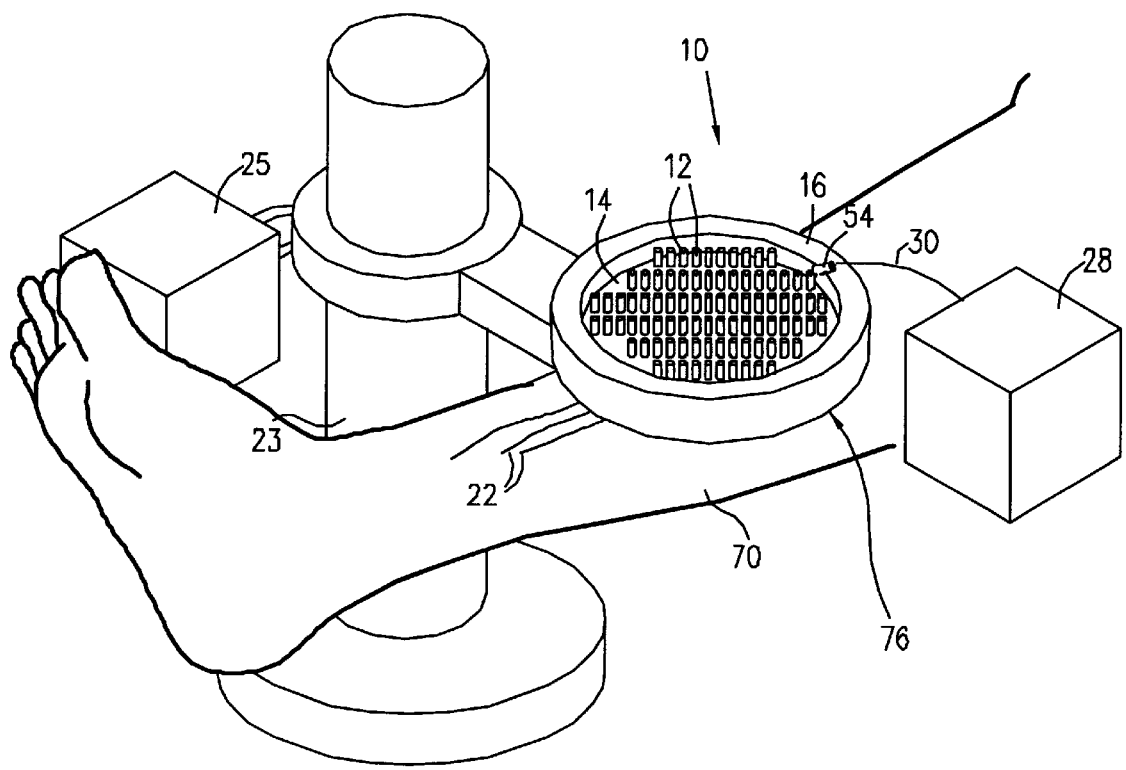
FIG. 2 is a simplified illustration of electrocoagulation apparatus constructed and operative in accordance with another preferred embodiment of the present invention.

Reference is now made to FIG. 1 which illustrates electrocoagulation apparatus 10, constructed and operative in accordance with a preferred embodiment of the present invention. Apparatus 10 includes an array of more than two RF energized needles 12 preferably mounted through a substrate 14 circumscribed by a ring 16. Ring 16 may include one or more straps 17 attachable to a limb of a patient. Alternatively, as shown in FIG. 2, ring 16 with needles 12 may be slidingly mounted on a stand 23 having control apparatus 25 for selectively plunging ring 16 and needles 12 against a limb of a patient at a site to be electrocoagulated.

Figure 3A:
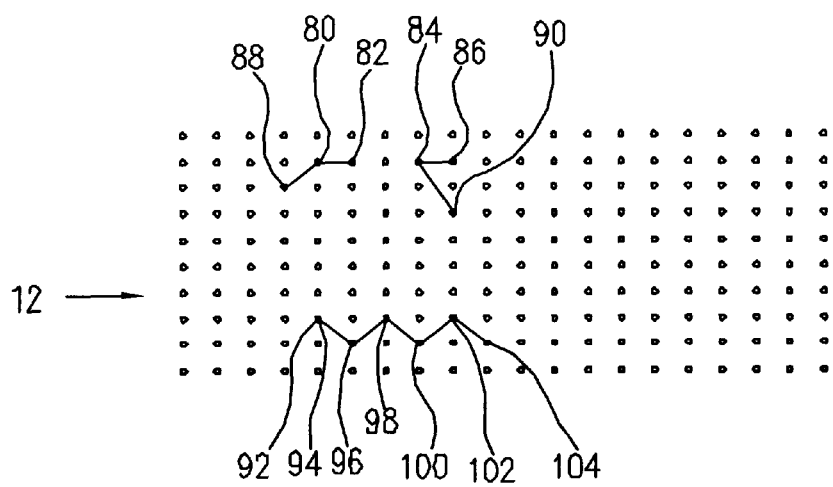
FIGS. 3A, 3B and 3C are simplified illustrations of different arrangements of needles of the electrocoagulation apparatus of FIG. 1 or FIG. 2.
Figure 3B:
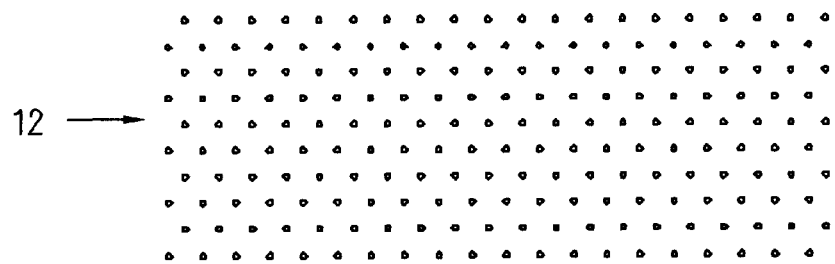
Figure 3C:
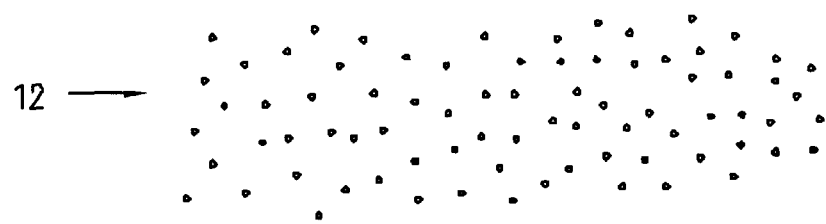

Needles 12 may be are arranged in any orderly or random fashion. Some possible arrangements are illustrated in FIGS. 3A–3C. For example, in FIG. 3A, needles 12 are arranged in rows generally aligned with each other to form an orderly matrix of rows and columns wherein needles 12 are generally equally spaced from each other. In FIG. 3B, needles 12 are arranged in staggered rows. In FIG. 3C, needles 12 are arranged in a random fashion.

Figure 4:
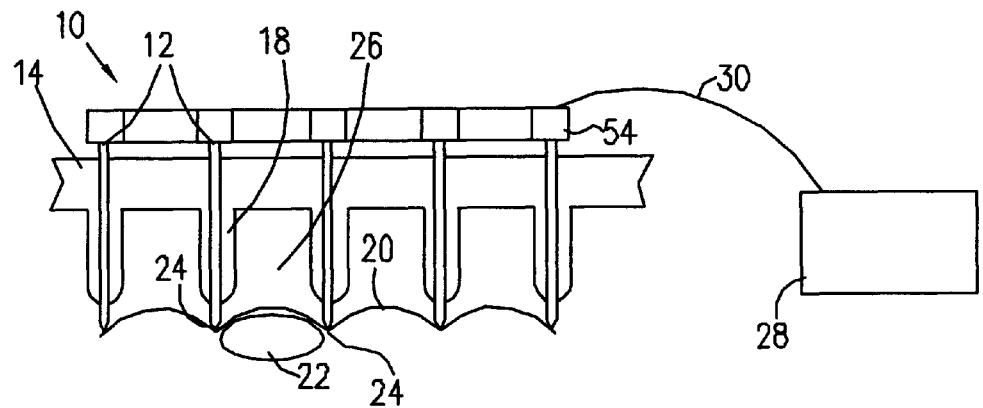
FIG. 4 is a simplified sectional illustration of the needles of the electrocoagulation apparatus of FIG. 1 or FIG. 2, taken along lines IV—IV in FIG. 1.

Reference is now particularly made to FIG. 4 which illustrates a section of substrate 14 with needles 12. Substrate 14 may include a plurality of protrusions 18 through which each needle 12 passes. Alternatively, substrate 14 may be generally flat with needles 12 passing therethrough. Needles 12 are preferably spaced from each other such that needles 12 may be pressed against epidermis 20 so as to cause a vein 22 to be located between tips 24 of adjacent needles 12. It is seen that needles 12 may be pressed against epidermis 20 so as to cause epidermis 20 to bulge inwards of a space 26 formed between tips 24. At least one of needles 12 may be hollow to allow passage therethrough of a substance, such as a coagulating agent or a substance which enhances electrical flow by lowering the local electrical resistance.

An RF generator 28 is preferably provided for selectively energizing at least two of needles 12 so that energy passes therebetween. As is known to persons skilled in the art, application of electrical power to a human body is preferably restricted to zero DC component power in order to avoid heart damage. RF generator 28 may be based on a TURAPY generator, commercially available from DIREX Ltd. of Petah Tikvah, Israel, preferably having the capability to modulate power with variably shaped pulses of a duration of 10 to 40 msec.

Tips 24 of needles 12 may be DIREX brand RF-needle tips. RF generator 28 is preferably collectively connected to needles 12 by an antenna wire 30. Antenna wire 30 is preferably made of 302 stainless steel, although other materials may be used. The length and connection of antenna wire 30 to RF generator 28 may be suitably chosen to meet certain design parameters, such as output impedance.

Needles 12 are preferably insulated over their whole length except for the last 0.5 mm. Antenna wire 30 is preferably connected to needles 12 by means of an RF connector 54, preferably located at least 20 mm from tips 24 for purposes of sterility. Alternatively, RF generator 28 may be connected individually to each needle 12 by individual RF connectors. Needles 12 are preferably disposable, and substrate 14 and/or ring 16 may also be disposable. Needles 12, once energized by RF generator 28, act as electrodes for electrocoagulating a site on a limb of a patient, as is now described hereinbelow with reference again to FIG. 2.

Ring 16 is fixed to a patient 70 at a site selected for electrocoagulation such as at a site of varicose veins 22 which appear as blue lines under the skin. Needles 12 straddle each vein 22 as shown and described hereinabove with reference to FIG. 4. A preferred target 76 is located at a site upstream of the blue lines, but where veins 22 are still visible. "Upstream" means between the vein and the heart.

RF generator 28 then transmits RF energy to veins 22 tips 24 to cause electrocoagulation of veins 22. Preferably the RF energy is in the form of a high frequency shaped train of pulses ("chirp"), typically, but not necessarily, in the range of 200 KHz to 1 MHz, and preferably with an intensity of up to 100 W. Preferably the duration of the pulses is approximately 10–40 msec, the duration changing in correspondence with the frequency and intensity of the pulses. RF energy may also be applied downstream of veins 22 in order to render same completely dry.

The RF energy may be transmitted to different pairs of needles 12 in a variety of manners. For example, referring to FIG. 3A, pairs of needles selected from the same row, such as needles designated by reference numerals 80 and 82 or 84 and 86. Alternatively, pairs of needles may be selected from different rows, such as needles designated by reference numerals 80 and 88 or 84 and 90. A zigzag pattern may be formed, for example, by energizing needles designated by reference numerals 92, 94, 96, 98, 100, 102 and 104. It is appreciated by persons skilled in the art that any other pattern may be energized. In this way, any pattern of varicose veins may be electrocoagulated, unlike the prior art which merely uses a pair of needles which may be ineffective in treating complicated clusters of varicose veins.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. Electrocoagulation apparatus comprising:
   a vein electrocoagulator comprising an array of more than two RF energized needles arranged in rows; and
   an RF generator for selectively energizing at least two of said needles so that energy passes therebetween, thereby being capable of producing electrocoagulation of veins.

2. Apparatus according to claim 1 wherein said rows are staggered.

3. Apparatus according to claim 1 wherein said needles are arranged in a matrix of rows and columns.

4. Apparatus according to claim 1 wherein said needles are generally equally spaced from each other.

5. Apparatus according to claim 1 wherein said needles are spaced from each other corresponding to the width of vein.

6. Apparatus according to claim 5 wherein said needles are attached to a ring which at least partially circumscribes said needles.

7. Apparatus according to claim 6 wherein said ring comprises a strap attachable to a limb of a patient.

8. Apparatus according to claim 1 wherein at least one of said needles is hollow to allow passage therethrough of a substance.

9. Apparatus according to claim 8 wherein said RF generator provides RF energy in the form of a chirp.

10. Apparatus according to claim 9 and wherein individual ones of said array of needles are energizable in a zigzag pattern.

11. Apparatus according to claim 9 and wherein said RF generator is operative for providing pulses of duration 10–40 msecs.

* * * * *